United States Patent [19]

Diamandis

[11] Patent Number: 5,854,008
[45] Date of Patent: Dec. 29, 1998

[54] EUROPIUM AND TERBIUM CHELATORS FOR THE TIME-RESOLVED FLUOROMETRIC ASSAYS

[75] Inventor: Eleftherios P. Diamandis, Toronto, Canada

[73] Assignee: Nordion International, Inc., Ontario, Canada

[21] Appl. No.: 313,300

[22] PCT Filed: Apr. 6, 1993

[86] PCT No.: PCT/CA93/00153

§ 371 Date: Dec. 21, 1994

§ 102(e) Date: Dec. 21, 1994

[87] PCT Pub. No.: WO93/20054

PCT Pub. Date: Oct. 14, 1993

Related U.S. Application Data

[63] Continuation-in-part of Ser. No. 863,746, Apr. 6, 1992, Pat. No. 5,312,922.

[51] Int. Cl.$^6$ .................. G01N 33/535; G01N 33/78; G01N 33/545
[52] U.S. Cl. .................. 435/7.91; 435/7.5; 436/500
[58] Field of Search .................. 435/7.91, 7.5; 546/156, 123; 544/354, 355, 258; 549/290, 289; 436/500

[56] References Cited

U.S. PATENT DOCUMENTS

| 5,095,099 | 3/1992 | Parkinson et al. ............... 534/15 |
| 5,312,922 | 5/1994 | Diamandis et al. .............. 546/156 |

FOREIGN PATENT DOCUMENTS

| 171978 | 2/1986 | European Pat. Off. |
| 191575 | 8/1986 | European Pat. Off. |
| 201211 | 11/1986 | European Pat. Off. |
| 290269 | 5/1987 | European Pat. Off. |
| 86/01604 | 3/1986 | WIPO |
| 91/08490 | 6/1991 | WIPO |

OTHER PUBLICATIONS

Chan et al., *Chem. Abst.*, 108:18763j.
Christopoulos et al., "Enzymatically Amplified Time-Resolved Fluorescence Immunoassay with Terbium Chelates", *Analyt. Chem.*, vol. 64, pp. 342–346 (1992).
Diamandis et al., Time–Resolved Fluorescence Using Europium Chelate 4,7-bis-(chlorosulfophenyl)1-, 10–phenanthroline–2,9–dicarboxylic acid (BCPDA), *J.Immunol.Meth.*, 112:43–52 (1988).
Evangelista et al., "Enzyme–Amplified Lanthanide Luminescence for Enzyme Detection in Bioanalytical Assays", *Anal. Biochem.*, v. 197, pp. 213–224 (1991).
Kallistratos, "Fluorescent Properties of Aromatic Complexes with Rare Earths and Other Elements of the IIIa–Group", *Chimika Chronika, New Series*, v. 11, pp. 249–266 (1982).
Khosravi et al., *Chem. Abst.*, 108:16385p.
Papanastasiou–Diamandi et al., "Ultrasensitive Thyrotropin Immunoassay Based on Enzymatically Amplified Time–Resolved Fluorescence with Terbium Chelate", *Clinical Chem.*, vol. 38, No. 4, pp. 545–548 (1992).
Chem. Abs. 115: 251258c (1991).
Chem. Abs. 115: 250720k (1991).
Chem. Abs. 112: 115231z (1990).
Chem. Abs. 113: 51733a (1990).
Chem. Abs. 106: 148547m (1987).
Chem. Abs. 118: 116868y (1993).
Kidani et al., "Studies on the Metal Complexes of Quinoxaline Derivatives. III. Metal Chelates of 2–Quinoxalinecarboxylic Acid and its N–oxides", *Bull. Chem Soc. Japan*, 47(8) 2040–2044 (1974).
J. Ye et al., Chemical Abstract No. 116: 161531 (1991). Luminescence properties of pyridinecarboxylic acid–europium(III) complexes.

*Primary Examiner*—Mary E. Ceperley
*Attorney, Agent, or Firm*—Banner & Witcoff, Ltd.

[57] ABSTRACT

Fluorogenic chelators for $Eu^{3+}$ and $Tb^{3+}$ are provided, they form highly fluorescent complexes with $Eu^{3+}$ and $Tb^{3+}$. In all cases, the fluorescence observed was lanthanide-specific, long-lived and it was monitored by microsecond time-resolved fluorometry. The fluorogenic chelators could be quantified, in the presence of excess lanthanide, at levels $<10^{-8}$ mol/L. Fluorogenic chelators can form ternary complexes with $Eu^{3+}$ and $Tb^{3+}$, in the presence of EDTA. The structures of the identified chelators is such that enzyme substrates can be used for enzyme-labelled time-resolved fluorometric immunoassays.

11 Claims, 9 Drawing Sheets

EUROPIUM AND TERBIUM CHELATORS FOR THE TIME-RESOLVED FLUOROMETRIC ASSAYS

This application is a continuation of Ser. No. 863,746 filed Apr. 6, 1992 now U.S. Pat. No. 5,312,922.

FIELD OF THE INVENTION

This invention relates to fluorescent lanthanide metal chelates and their use in diagnostics.

BACKGROUND OF THE INVENTION

In order to facilitate discussion of known fluorescent entities, their application and the manner in which the fluorescent entities in this invention distinguish from known systems, reference will be made to several scientific articles throughout the specification. To facilitate such reference the articles have been listed by number as follows:

1. Diamandis, E. P. Clin. Biochem. 1988, 21, 139–150.
2. Diamandis, E. P. Clin. Chim. Acta. 1990, 194,19–50.
3. Diamandis, E. P.; Christopoulos, T. K. Anal. Chem. 1990, 62, 11 49A-11 57A.
4. Soini, E.; Lovgren, T. CRC Crit. Rev. Anal. Chem. 1987, 18, 105–154.
5. Hemmila, I.; Dakubu, S.; Mukkala V. M.; Siitari, H.; Lovgren, T. Anal. Biochem. 137, 335–343.
6. Soini, E.; Kojola, H. Clin. Chem. 1983, 29, 15–68.
7. Evangelista, R. A.; Pollak, A.; Allore, B.; Templeton, E. F.; Morton, R. C.; Diamandis, E. P. Clin. Biochem. 1988, 21, 173–178.
8. Diamandis, E. P.; Morton, R. C.; J. Immunol. Method 1988, 12, 43–52.
9. Bailey, M. P.; Rocks, B. F.; Riley, C. Analyst 1984, 109, 1449–1450.
10. Oser, A.; Gollasius, M.; Valet, G. Anal. Biochem. 1990, 191, 295–301.
11. Hemmila, I.; I Hoittinen, S.; Pettersson, K.; Lovgren, T. Clin. Chem. 1987, 33, 2281–2283.
12. Sinha, A. P. B. Spectrosc. Inorg. Chem. 1971, 2, 255–265.
13. Kallistratos, G. Chimica Chronica New Series, 1982, 11, 249–266.
14. Diamandis, E. P.; Morton, R. C.; Reichstein, E.; Khosravi, M. J. Anal. Chem. 1989, 61, 48–53.
15. Morton, R. C.; Diamandis, E. P. Anal. Chem. 1990, 62, 1841–1845.
16. Diamandis, E. P. Clin. Chem. 1991, 37, 1486–1491.
17. Evangelists, R. A.; Pollak, A.; Gudgin-Templeton, E. F. Anal. Biochem. 1991, 197, 213–224.
18. Christopoulos, T. K.; Diamandis, E. P. Anal. Chem. 1992, (in press).
19. Papanastasiou-Diamandis, A.; Christopoulos, T. K.; Diamandis, E. P. Clin. Chem. 1992 (in press).
20. Papanastasiou-Diamandis, A.; Bhayana, V.; Diamandis, E. P. Ann. Clin. Biochem. 1989, 26, 238–243.
21. Fenley, H. N., Walker, P. G., Biochem. J. 1965, 97, 95–103.

Fluorescent lanthanide metal chelates and in particular those for europium and terbium chelates have significant commercial application because of their use as labels in highly sensitive time-resolved fluorometric immunoassays (1–4). The first commercially available time-resolved fluorescence immunoassay system, Delfiae® (available by Pharmacia-LKB, Sweden) uses $Eu^{3+}$ as immunological label (5,6). A second-generation time-resolved fluorometric immunoassay system, FlAgene® (available by CyberFluor Inc., Toronto, Canada, the applicant in this application) uses the europium chelator 4,7-bis (chlorosulfophenyl)-1,10-phenanthroline-2,9-dicarboxylic acid (BCPDA) as immunological label (7.8). These two systems, along with the principles of time-resolved fluorometry and its application to immunoassay and other bioanalytical techniques have been investigated in detail (1–4).

Recently, $Tb^{3+}$ and its chelates have been used as immunological and nucleic acid labels (9,10). In general, $Tb^{3+}$ is inferior to $Eu^{3+}$ in terms of detectability. However, $Eu^{3+}$ and $Tb^{3+}$ can be used simultaneously for dual analyte assays (11).

The mechanism of fluorescence of the $Eu^{3+}$ and $Tb^{3+}$ chelates has been described (1–4). These two ions, when excited by radiation, emit very weak metal ion fluorescence which is not analytically useful. The fluorescence is dramatically enhanced when the metal ion forms a chelate with appropriate organic ligands. An important property of these chelates is that the radiation is absorbed at a wavelength characteristic of the ligand and is emitted as a line spectrum characteristic of the metal ion. This is due to an intramolecular energy transfer from the ligand to the central metal ion (12). In general, it is difficult to predict theoretically which organic molecules-ligands can form highly fluorescent complexes with lanthanide metals, and in particular, with $Eu^{3+}$ and $Tb^{3+}$. Some classes of compounds i.e. the diketones, tetracyclines, phenanthrolines, acetylene derivatives, five-membered heterocyclic ring derivatives, benzoic acid derivatives, biphenyl derivatives, pyridine derivatives, pyrimidine and pyrazine derivatives, di-and tripyridyl derivatives, quinoline derivatives, aza-uracil and purine derivatives and phosphorimido-derivatives have been identified as fluorogenic ligands of $Eu^{3+}$ and/or $Tb^{3+}$ (13).

In time-resolved fluorometric immunoassays, it is desirable to use a chelate-label which can be detected down to the subpicomolar range (5). Alternatively, multiple labelling strategies can be used in order to achieve subpicomolar analyte sensitivity (1 and 4–16). More recently, there have been efforts to combine time-resolved fluorometric immunoassay with enzymatic catalysis. In one version of this approach, the primary immunological label is alkaline phosphatase (ALP); its substrate is the phosphate ester of 5-fluorosalicylic acid (FSAP). The nonhydrolysed ester (FSAP) and the hydrolysed ester (FSA) have different behaviour in $Tb^{3+}$-EDTA solutions. When FSA is added to an aqueous alkaline solution containing $Tb^{3+}$-EDTA, a mixed complex is formed which emits long-lived fluorescence characteristic of $Tb^{3+}$. FSA is an appropriate ligand for energy transfer to the metal ion. An intact hydroxyl group on the FSA molecule is essential for these highly fluorescent mixed complexes to be formed. FSAP does not form any fluorescent complexes with $Tb^{3+}$-EDTA. In a heterogeneous immunoassay design, ALP activity can be monitored with use of FSAP as substrate, by measuring the released FSA after adding an alkaline solution of $Tb^{3+}$-EDTA (17). This system has been used for the highly sensitive and rapid quantification of alpha-fetoprotein and thyrotropin in serum (18,19).

SUMMARY OF THE INVENTION

According to an aspect of the invention, fluorescent lanthanide metal chelates are selected from compounds of the following formulas I through X:

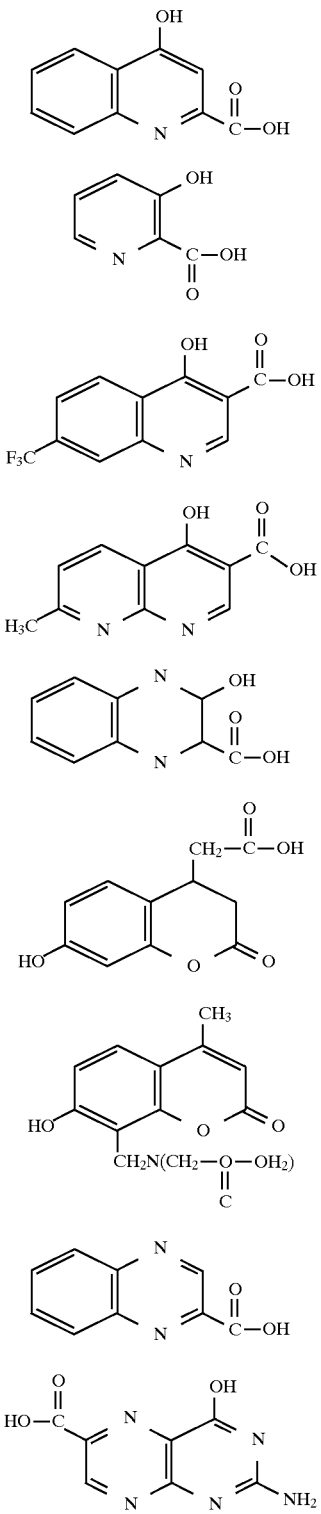

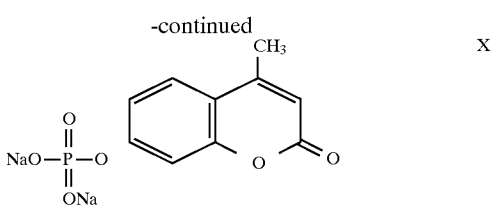

According to another aspect of the invention, in a time resolved fluorescent based assay, the selected esters of chelates of formulas I through X are enzymatically treated to render the chelates either fluorescent or non-fluorescent when combined with a selected lanthanide metal.

BRIEF DESCRIPTION OF THE DRAWINGS

Preferred embodiments of the invention are discussed with respect to the following drawings wherein.

DETAILED DESCRIPTIONS OF THE PREFERRED EMBODIMENT

Figure 1A:
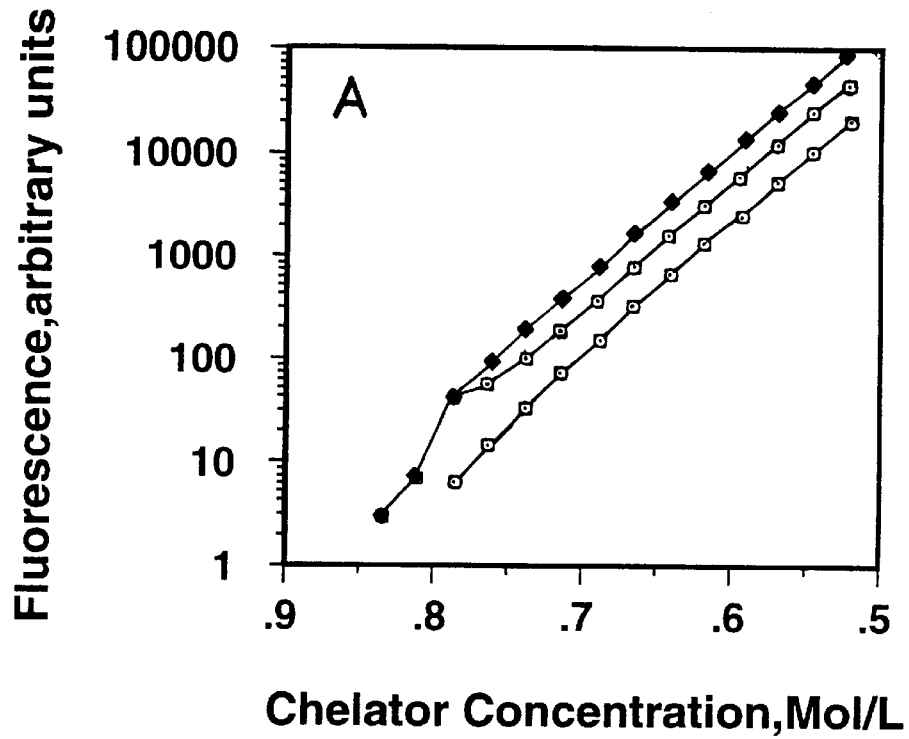
FIG. 1. Logarithmic plots of fluorescence vs concentration of candidate fluorogenic lanthanide chelator. In all cases A to E but D, the fluorescence of each $Eu^{3+}$ chelate was higher or equal (C) to the corresponding fluorescence of the $Tb^{3+}$ chelate; the $Eu^{3+}$-chelate fluorescence curve in plots A to E is thus on top of the $Tb^{3+}$-chelate fluorescence curve, except in case D. The chelators represented are III (A, the third curve representing the lowest fluorescence is due to the $Tb^{3+}$-EDTA-fluorosalicylate complex as described in (17); IV (B); II (C); VII (D); X (E); I (F, with $Eu^{3+}$); V (G, with $Eu^{3+}$); VI (H, with $Eu^{3+}$); VIII (I, lower curve with $Eu^{3+}$); IX (I, upper curve with $Eu^{3+}$).
Figure 1B:
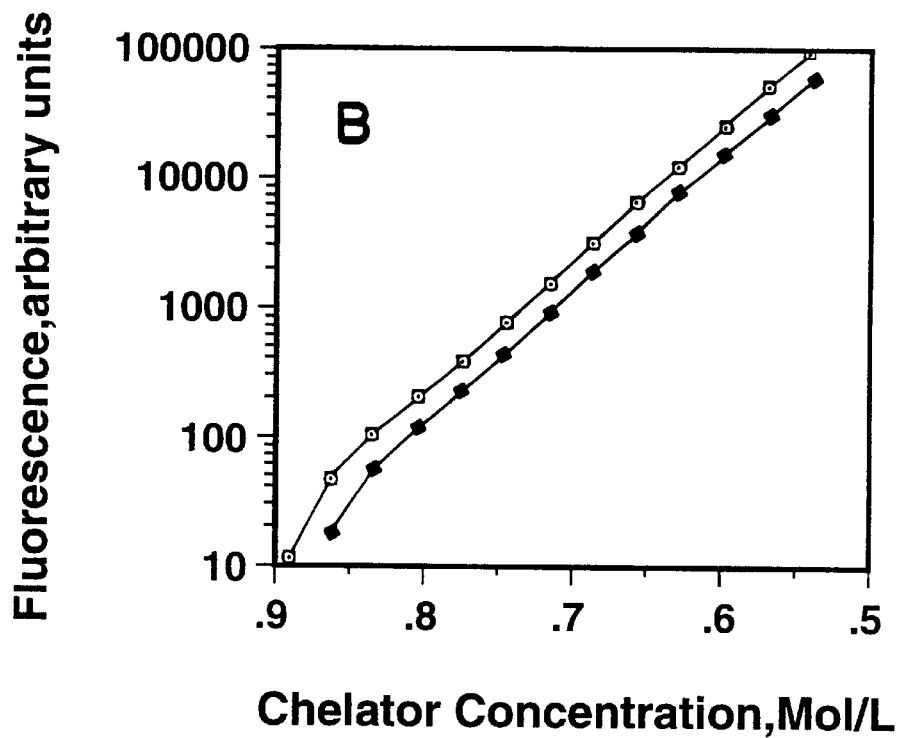
Figure 1C:
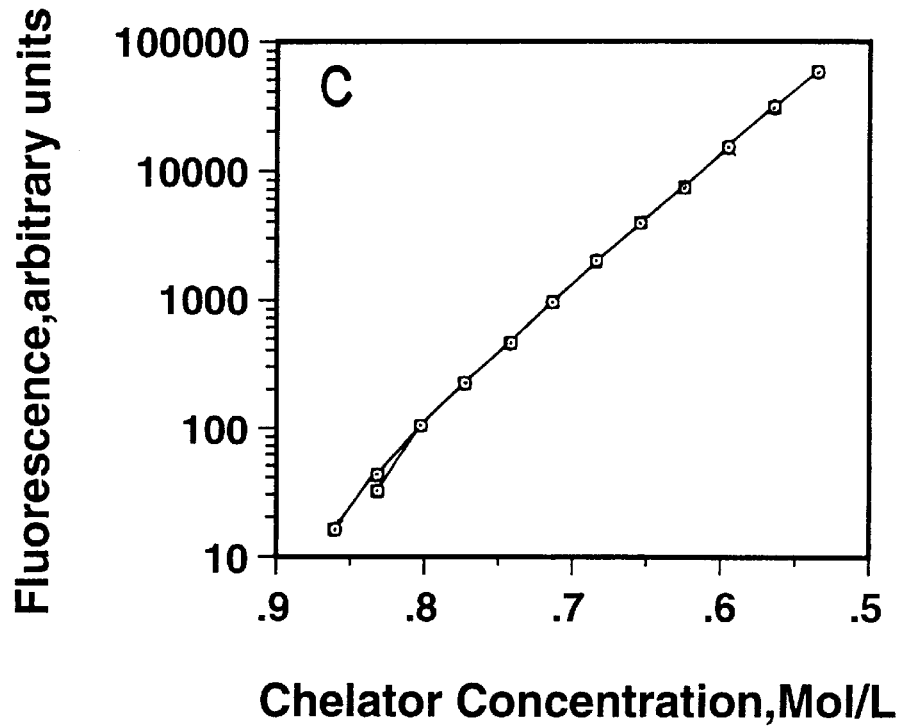
Figure 1D:
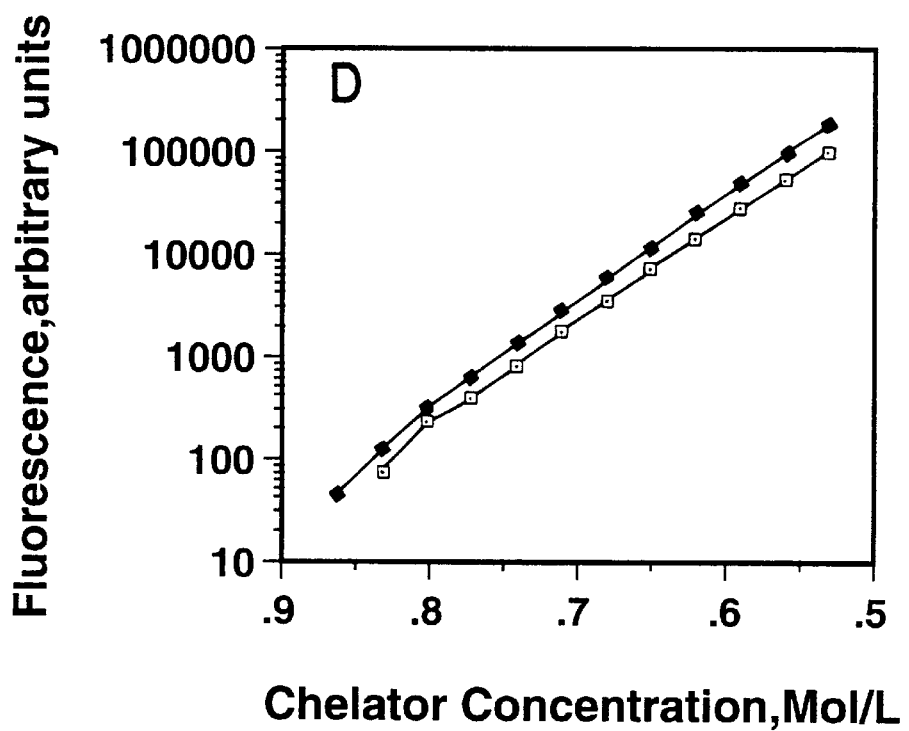
Figure 1E:
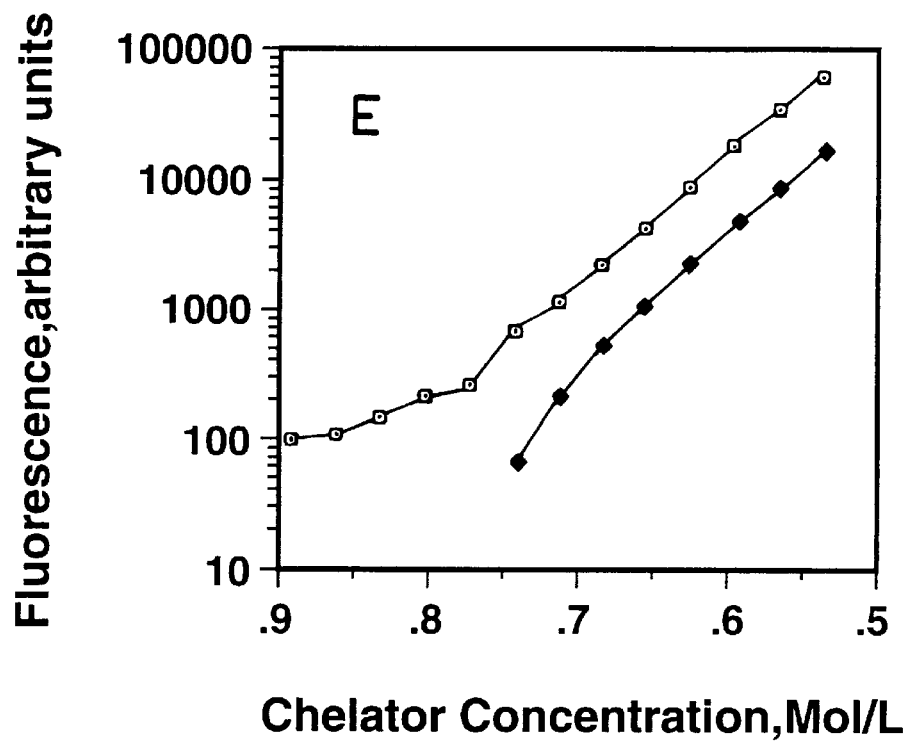
Figure 1F:
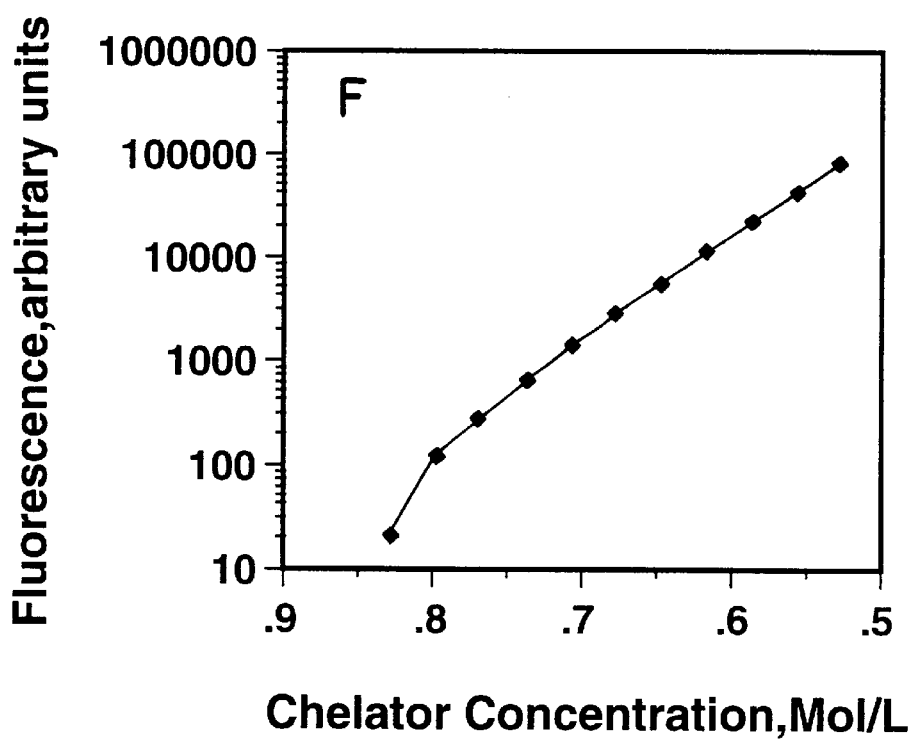
Figure 1G:
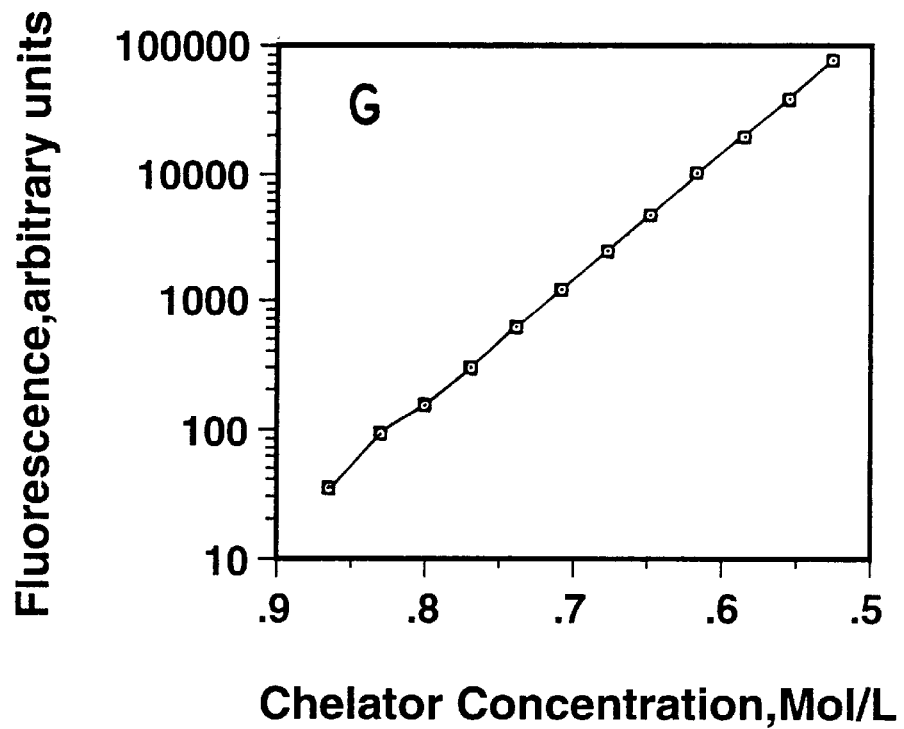
Figure 1H:
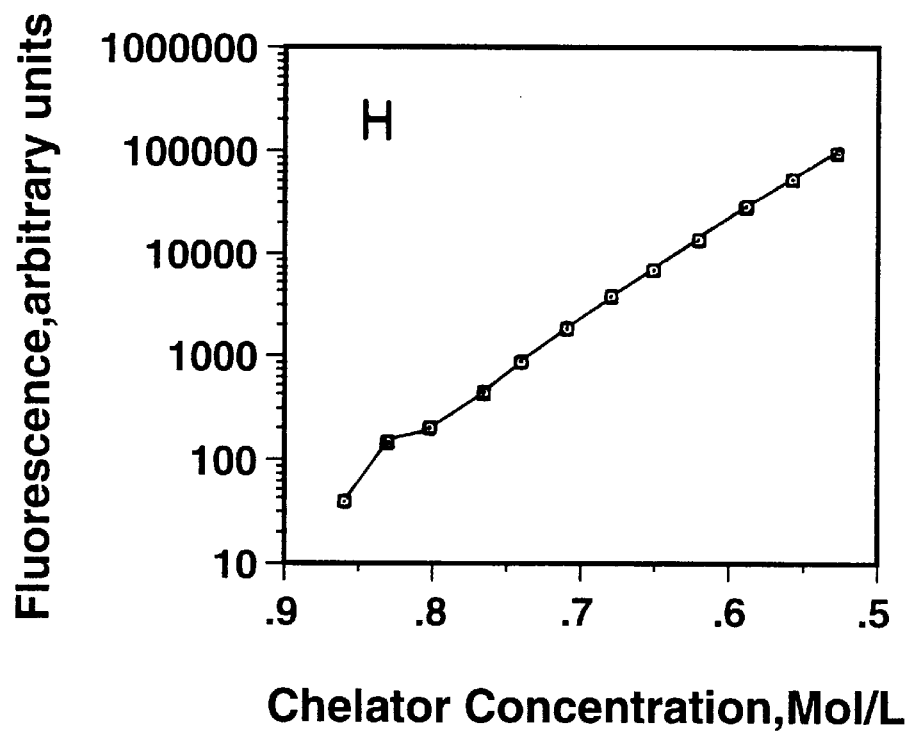
Figure 1I:
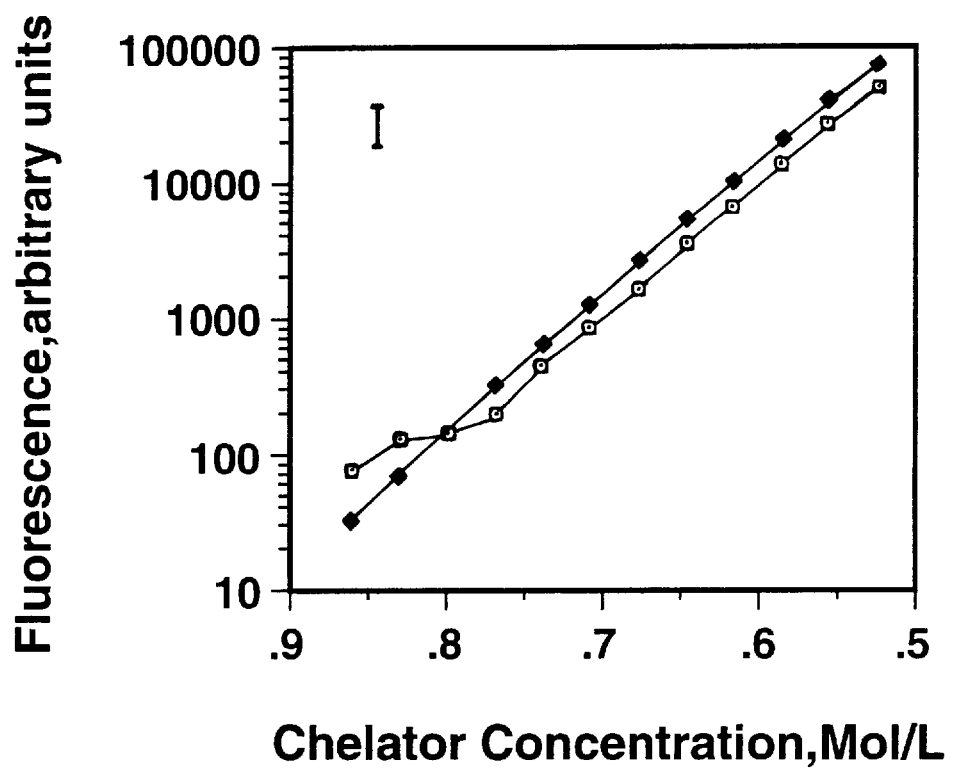

Examination of this and other enzyme immunoassay systems reveals that immunological assays with subpicomolar analyte sensitivity and speed can be developed if the substrate (i.e. FSA) can be quantified at a concentration level of $\sim 10^{-8}$M. The analyte detectability at levels $< 10^{-12}$M is due to the enzymatic amplification introduced by ALP or other enzymes.

Several compounds which provide $Eu^{3+}$ and/or $Tb^{3+}$ fluorogenic chelators have been identified. These molecules have two criteria in common: (a) that their structure contains aromatic or heteroaromatic rings capable of absorbing electromagnetic radiation which internally excites the lanthanide and, (b) that the structure contains a lanthanide binding site which preferably but not necessarily consists of at least one carboxyl group and a hydroxyl group; the hydroxyl group being available for conversion to either a phosphate ester or a galactoside. These derivatives can also act as substrates for alkaline phosphatase or β-galactosidase, respectively.

The molecules are identified as follows in formulas I through X:

TABLE 1

Optimal Assay Conditions of Chelators in the Presence of $Eu^{3+}$ or $Tb^{3+}$

| | Works in presence of EDTA? | Detection Limit, Mol/L | Stability of Fluorescence | pH optimum[2] |
|---|---|---|---|---|
| Europium Chelator | | | | |
| I | No | $5 \times 10^{-9}$ | Poor | 11 |
| II | No | $5 \times 10^9$ | Good | 9–11 |
| III | Yes | $2 \times 10^{-9[1]}$ | Good[1] | 11[1] |
| IV | Yes | $2 \times 10^{-9[1]}$ | Good[1] | 11[1] |
| V | No | $2.5 \times 10^{-9}$ | Good | 11 |
| VI | No | $2.5 \times 10^{-9}$ | Poor | 9–11 |
| VII | No | $4 \times 10^{-9}$ | Good | 9–11 |
| VIII | No | $7 \times 10^{-9}$ | Poor | 11 |
| IX | No | $2.5 \times 10^{-9}$ | Good | 9–11 |
| X | No | $2.5 \times 10^{-9}$ | Poor | 9–11 |
| Terbium Chelator | | | | |
| II | No | $5 \times 10^{-9}$ | Good | 11 |
| III | Yes | $3 \times 10^{-9[1]}$ | Good[1] | 11[1] |
| IV | Yes | $5 \times 10^{-9[1]}$ | Good[1] | 11[1] |
| VII | No | $2 \times 10^{-9}$ | Good | 11 |
| X | No | $3.9 \times 10^{-9}$ | Poor | 11 |

[1]Studies done in the presence of $Eu^{3+}$ or $Tb^{3+}$ and EDTA

The registry numbers for these compounds are as follows:
- I, 4-hydroxy- quinoline-2-carboxylic acid, 492-27-3;
- II, 3-hydroxypicolinic acid, 874-24-8;
- III, 4-hydroxy-7-trifluromethyl-3-quinoline carboxylic acid, 574-92-5;
- IV, 4-hydroxy-7-methyl-1,8-naphthyridine-3-carboxylic acid, 13250-97-0;
- V, 3-hydroxy-2-quinoxaline carboxylic acid, 1204-75-7;
- VI, 7-hydroxycoumarin-4-acetic acid, 6950-82-9;
- VII, calcein blue, 54375-47-2;
- VIII, 2-quinoxaline carboxylic acid, 879-65-2;
- IX, Pterin-6-carboxylic acid, 948-60-7;
- X, 4-methylumbelliferyl phosphate, sodium salt, 22919-26-2.

Molecules II, III, IV, and VII of the above formulae are good fluorogenic chelators for both $Eu^{3+}$ and $Tb^{3+}$ and molecules II, III, IV, V, VII and IX of the above formulae are good fluorogenic chelators for $Eu^{3+}$. Under optimised measuring conditions of pH and presence or absence of EDTA, these chelators can be detected at levels<$10^{-8}$M. Thus, these substrates demonstrate utility in highly sensitive enzymatically amplified time-resolved fluorometric immunoassays. One chelator identified, 4-methylumbelliferyl phosphate of formula X, which is a substrate for alkaline phosphatase, was used as a model to develop new heterogeneous time-resolved fluorescence immunoassays for thyrotropin (TSH) and thyroxine (T4) in serum.

In the present invention high detection sensitivity signal generation is achieved in a method for enzymatically amplifying signal detection through utilization of a selected substrate which is capable of being transformed by an enzyme from a compound which does not form a luminescent lanthanide chelate into a chelator which forms a luminescent lanthanide chelate with a lanthanide metal ion. This may occur in the presence or absence of a co-chelator. The substrate selected in unconverted form is non-competitive with the lanthanide metal chelate when exposed to radiation which causes the lanthanide metal chelate to luminesce. For example, the selected substrate may have a degree of luminescence in the presence of the lanthanide metal. It is understood, however, that such luminescence from the substrate does not interfere with the luminescence signal from the lanthanide metal ion chelate. This may be due to the luminescent emission from the substrate occurring at a different time than the emissions from the lanthanide metal chelate or may also be due to the emission from the substrate being considerably weaker than the emission occurring at the same time from the chelate or the substrate may be excited at a wavelength which is substantially different from that of the chelate. Any luminescence from the substrate, should it exist or not exist, results in a selected substrate which is hence non-competitive during the luminescent detection step with the lanthanide metal chelate.

The luminescent lanthanide chelate thus formed is detected using either normal or time-resolved luminescence methods. This detection system can be utilized in many different heterogeneous assay formats, including microtitration plate formats for immunoassays and dot blot or Southern blot formats for hybridization assays. In addition, it may be utilized for a variety of homogeneous, heterogeneous or in situ assay formats and for specific enzyme activity.

In accordance with an aspect of the present invention a new method is provided for detection and/or quantification of an enzyme, where the enzyme is either used as a labelling group (for example bound to a hapten, antibody, binding protein, plant lectin, carbohydrate, hormone, or nucleic acid), or is itself the analyte of interest. In this method a substrate is enzymatically converted from a compound which under the conditions of the luminescence measurement does not form a highly luminescent chelate with a lanthanide ion to a product (chelator) which does form such a luminescent lanthanide chelate.

The necessary alteration in the luminescent properties of the product, resulting in a substantially increased yield of luminescent lanthanide complex formation on conversion from the substrate, may be due to any combination of one or more of the following factors: more efficient net energy transfer from the product to the lanthanide ion in the chelate; more efficient light absorption by the product lanthanide chelate than for the substrate lanthanide chelate due to an alteration of spectroscopic properties energy levels; or, an increase in the number of groups coordinated to the lanthanide in the product compared to the substrate as a result of enzymatic action, for example due to addition of new coordinating groups, coupling of two species each containing coordinating groups, alteration of existing poorly coordinating groups to strongly coordinating groups, or removal of blocking groups in the vicinity of the chelating site which may hinder complex formation, any of which can result in a higher binding constant for the formation of complexes of the product with the lanthanide, and a higher yield of luminescence due to exclusion from the coordination sphere of the lanthanide of water molecules which are known to quench the luminescence of some lanthanides.

The complexes formed between the product and the lanthanide may be of any stoichiometry; in particular complexes of the type 1:n lanthanide:product (n=1 to 3) are preferred. In addition, the complex may contain other coordinating species present in the solution, such as buffer ions or ethylenediaminetetraacetate (EDTA) ion, which enhance the luminescence of the product:lanthanide chelate. Thus, in this invention, the principles of enzymatic amplification and time-resolved luminescence of lanthanide chelates are combined in order to give the higher sensitivity provided by the utilization of both signal amplification and background rejection.

In addition, the method of the present invention can be applied to detection of a wider variety of enzymes than are currently used for other forms of detection, due to the large number of possible enzymatic reactions resulting in a significant alteration of the chelating or spectroscopic properties of the substrate. This imparts the advantage of improved background rejection compared to normal fluorophores, allowing improved detection limits for the enzyme. This is based on the specific luminescence properties of the lanthanide chelates which permit practical and inexpensive wavelength filtering and time-gating to be performed during the measurement in order to detect only the luminescence of the lanthanide chelate.

In the present invention, the chelating agent is not directly attached as a labelling group. The present invention is differentiated from other luminescence methods for the detection or quantitation of specific enzymes where the enzyme is the analyte, in that the luminescence of the enzymatic product itself is not measured, rather the luminescence of the complex formed between the product and a lanthanide ion is quantitated. Examples of suitable lanthanides include, but are not limited to, terbium, europium, samarium and dysprosium. The amplification by the enzyme coupled with the lanthanide-chelate luminescence imparts the advantage of improved background rejection as compared to normal fluorophores thereby permitting improved detection limits for the enzyme. It is recognized in the present invention that it is the specific luminescence properties of the lanthanide chelates which permit practical and inexpensive wavelength filtering and time-gating to be performed during the measurement in order to detect only the luminescence of the lanthanide chelate.

Another aspect of the present invention lies in the use of an enzyme as a label, or analyte, which reacts with the selected substrate to produce a non-chelator product which can subsequently react with a compound not capable of forming a luminescent lanthanide chelate, in order to form a second product chelating agent capable of forming such a chelate.

In addition, the invention can be utilized for assay formats in which the labelling group is a first enzyme which produces a cofactor or substrate used by a second enzyme present in solution to subsequently produce the desired product capable of luminescent lanthanide chelate formation, or for a format in which a first enzyme produces an inhibitor for such a second enzyme, causing a reduction in measured signal when the first enzyme is present. The method is suitable for use in any assay format in which quantitation of the amount of enzyme present is appropriate. This includes many types of separation immunoassays or hybridization assays wherein the enzyme is used as a label on a hapten, protein or nucleic acid fragment, as examples, which when bound to its specific antibody, hapten or complementary nucleic acid sequence can be separated from unbound species. The enzyme may be directly or indirectly, covalently or noncovalently bound, and present as a single or multiple label. Such formats include the enzyme-linked immunosorbent assay, dot-blot, Southern blot or sandwich hybridization assays, in situ hybridization or immunoassays, and gel permeation separation assays. The luminescent product may be detected in solution, deposited onto a solid support, or suspended in an inhomogeneous matrix such as an electrophoretic gel.

Examples of known assay methodologies and reagents used in these assays are detailed in the following patents: EP 0 192 168 (Dattagupta), EP 0 146 815 (Albarella & Anderson), EP 0 146 039 (Albarella et al.), WO 84/04970 (Ward et al.), WO 87/03622 (Schneider & Shank), EP 0 138 357 (Landes), and EP 0 131 830 (Dattagupta). All of these methodologies may be adapted by the method of the present invention.

In addition, the method is suitable for use in assays for specific enzymes, with the choice of a suitable substrate, in order to establish the presence, specificity or specific activity of a particular enzyme in a sample, for example, in tissue, either homogenized or in section, in cell cultures, or immobilized on a solid support. The enzyme whose activity or concentration is to be determined may be present in other biological tissue samples such as whole blood, plasma or serum. Alternatively, the enzyme may be directly or indirectly conjugated to antibody which is part of the immunological complex in an immunoassay, present as an enzyme which is directly or indirectly conjugated to a nucleic acid probe which is part of a DNA-DNA or DNA-RNA duplex in a nucleic acid hybridization assay, or, by suitable means, the enzyme is immobilized on to a solid support. As such, the invention, is equally applicable to DNA sequencing techniques as well as DNA probes.

The enzymatic reaction step of the present invention need not be performed under the same reaction conditions as the conditions for the formation of the lanthanide chelate and measurement of the luminescence. The lanthanide, and any co-chelating agents, such as EDTA, may be present during the enzymatic reaction or may be added subsequently. The pH of the solution may also be altered to improve complex formation. The luminescence of the product chelate is measured under conditions intended to optimize discrimination against any small background signals. The measurement of the luminescence may be performed under conditions of continuous illumination with ultraviolet light, with an excitation wavelength filter chosen to excite preferentially the product/lanthanide chelate over the substrate if possible, and an emission wavelength filter chosen to select for the lanthanide emission. Preferably, the measurement is performed using, in addition to the aforementioned wavelength filtering, pulsed ultraviolet excitation and time-gated detection optimized with respect to the luminescence lifetime of the chelate; this method of measurement provides the best discrimination against nonspecific background luminescence signals.

A number of enzyme-protein and enzyme-nucleic acid conjugates are commercially available or have been reported in the literature and can be used by a person skilled in the art with the method and reagents of the present invention.

In order to demonstrate the fluorescent capabilities of the various chelators, the following experimental section is provided as a technical guide for investigating the fluorescent properties of preferred chelators.

Instrumentation

All time-resolved fluorometric measurements were carried out in white polystyrene microtiter wells obtained from Dynatech Laboratories, Alexandria, Va., using the 615® Immunoanalyzer. This instrument is a microsecond time-resolved fluorometer commercially available by CyberFluor Inc., Toronto, Canada. The emission filter used, at 615 nm, was found suitable for both $Eu^{3+}$ and $Tb^{3+}$, as previously described (18). The excitation source is a nitrogen laser providing excitation radiation at 337.1 nm. No effort was made to optimize the excitation wavelength for each chelator tested.

Chemicals and Solutions

The candidate organic chelators tested are shown in FIG. 1. All of them were obtained from Aldrich Chemical Co., Milwaukee, Wis. 53233. Calf intestine alkaline phosphatase (ALP) was obtained from Boehringer Mannheim Canada, Montreal PQ. Alkaline phosphatase-labelled streptavidin (SA-ALP) was obtained from Zymed Laboratories Inc., San Francisco, Calif. 94080, as a 0.75 mg/mL solution. White, opaque 12-well polystyrene microtiter strips coated with monoclonal anti-thyrotropin antibody (for the TSH assay) or a thyroxine-globulin conjugate (for the T4 assay) were obtained from CyberFluor. The biotinylated detection antibodies, standards and buffers needed for the immunoassays were also from CyberFluor. Europium (III) chloride hexahydrate and terbium (III) chloride hexahydrate were from Aldrich. All other chemicals were from Sigma Chemical Co., St. Louis, Mo. 63178.

All chelators were dissolved in a 0.1 mol/L Tris buffer, pH 9.0, to prepare stock $10^{-3}$ mol/L solutions. More dilute solutions were prepared in the same buffer as needed. The alkaline phosphatase substrate buffer was a 0.1 mol/L Tris, pH 9.0, containing 0.1 mol/L NaCl and 1 mmol/L $MgCl_2$. The diluent for the biotinylated detection TSH antibody and the SA-ALP conjugate was a 6% (w/v) solution of bovine serum albumin (BSA) in a 50 mmol/L Tris buffer, pH 7.40, containing 0.5 g of sodium azide per liter. The wash solution was prepared by dissolving 9 g of NaCl and 0.5 mL of polyoxyethylenesorbitan monolaurate (Tween 20) in 1 liter of distilled water.

Procedures

All chelators were screened by mixing 100 μL of a chelator solution and 100 μL of a $Eu^{3+}$ or $Tb^{3+}$ solution, ($4\times10^{-3}$ mol/L in water) and measuring the delayed fluorescence on the 615® Immunoanalyzer. The chelators according to preferred embodiments of the invention were further tested with $Eu^{3+}$ or $Tb^{3+}$ solutions of various pH, in the absence or presence of EDTA. Calibration curves and detection limits were constructed or calculated by adding 100 μL of an aqueous $Eu^{3+}$ or $Tb^{3+}$ solution to 100 μL of a chelator solution in a 0.1 mol/L Tris buffer of pH 9.0. For the FSA chelator, we added 100 μL of a $Tb^{3+}$-EDTA solution, $10^{-3}$ mol/L in a 0.5 mol/L Tris buffer (18) of pH 12.5. For chelators of formula III and IV, we added 100 μL of a $4\times10^{-3}$ mol/L solution of $Eu^{3+}$ or $Tb^{3+}$ in a 0.1 mol/L Tris buffer, pH 11, containing $5\times10^{-3}$ mol/L EDTA.

EXAMPLE 1

Immunoassay of TSH

Pipet 100 μL of TSH standards (0, 0.25, 0.50, 1, 2, 4, 8, and 16 mU/L) into monoclonal antibody-coated wells and then add 50 μL of biotinylated monoclonal detection antibody diluted 50-fold in the 6% BSA diluent. Incubate with mechanical shaking for 1 h at room temperature and wash× 4. Add 100 μL/well of the SA-ALP conjugate diluted 3000-fold in the 6% BSA diluent, incubate 15 min as above and wash×4. Add 100 μL/well of the 4-methylumbelliferyl phosphate substrate diluted to a concentration between $5\times10^{-6}$–$5\times10^{-5}$ M in the alkaline phosphatase substrate diluent and incubate as above for 30 min. Then, add 100 μL of a $Eu^{3+}$ solution, $4\times10^{-3}$ M in water, mix and measure fluorescence within 5 min with the 615™ Immunoanalyzer. The calibration curve and data reduction are carried out automatically by the analyzer.

EXAMPLE 2

Immunoassay of T4

Pipet 10 μL of thyroxine standards or serum samples into thyroxine-coated wells and then add 100 μL of biotinylated T4 antibody diluted 20-fold in the T4-antibody diluent. Incubate with mechanical shaking for 1 h at room temperature and wash×4. Add 100 μL/well of the SA-ALP conjugate and complete the assay as described for TSH but substrate incubation is only 15 min.

EXAMPLE 3

Preparation of the Phosphate Ester of 4-hydroxy-7-trifluoromethyl-3-quinoline carboxylic acid (HTOCP)

Figure 5:
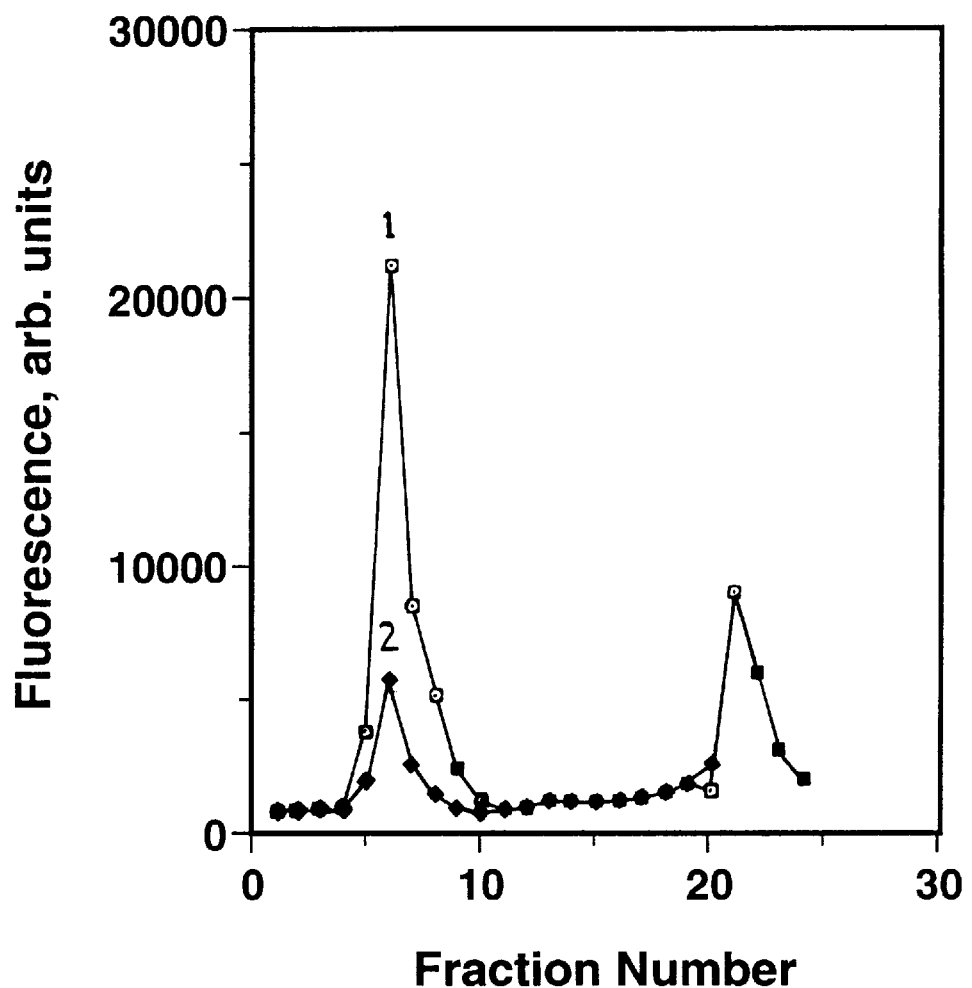
FIG. 5. Enzymatic hydrolysis of the HTQCP phosphate in Fraction 6 by alkaline phosphatase. Compound HTQC elutes as well in Fraction 21. Line (1) is with enzyme alkaline phosphatase and Line (2), no enzyme added.

The method described by Fernley and Walker (21) was used. HTQC (10 g) (Chelator III) in pyridine (20 mL) was added with stirring to a cooled mixture of phosphoryl chloride (8.5 g) in pyridine (40 mL) such that the temperature remained below 5° C. After 30 min., the reaction mixture was decomposed by the addition of ice-cold water (100 mL). The solution was adjusted to pH 7.5 with 10M NaOH and solvents were removed under reduced pressure. The product, HTQCP, was purified by C18-reverse-phase, high performance liquid chromatography using a mobile phase of 10% acetonitrile in water and increasing it to 40% in 20 min. using a linear gradient (flow-rate 1 mL/min). One mL fractions from the HPLC separation were collected and tested for enzymatic activity as follows. In white microtiter wells (Dynatech) add 100 μL of substrate buffer (0.1 mol/L Tris, pH 9.1, containing 0.15 mol NaCl and 1 mmol of $MgCl_2$ per liter) and 10 μL of each HPLC fraction in duplicate. In one of the duplicate wells, add 1 μL of an alkaline phosphatase enzyme solution (from Boehringer Mannheim) and incubate for 10 min, shaking at room temperature. In all wells add 100 μL of a $10^{-3}$ mol/L $EuCl_3$-EDTA solution, pH 11.0, and measure the fluorescence with the Cyberfluor 615® Immunoanalyzer. Results are shown in FIG. 5. It can be seen that there is alkaline phosphatase substrate activity in Fraction #6. When the HTCQP is reacted with alkaline phosphatase, the product, HTCQ, has a greater fluorescence as shown by peak 1. The parent compound, HTQC, elutes in Fraction #21 and its fluorescence is not changed by the presence of the enzyme. Similar results were obtained with the terbium chelator calcein blue phosphate (CBP, VII).

Results and Discussion Based on the Experimental Procedure

Many chelators of the formulae possess a hydroxyl group which could be converted to a phosphate ester or galactoside for the purpose of using them as substrates of alkaline phosphatase or β-galactosidase as has already been reported for the chelator of FSA which is included for comparison (17–19). In some cases, sets of candidate chelators with only one group difference were tested i.e. chelators of formulae V and VIII, to demonstrate the importance of the different groups. Derivatives of a particular structure i.e. 4-methylumbelliferone (formulae VI, VII and X) and quinoline derivatives (formulae I and III) were tested. From the structures of the formulae ten compounds form highly fluorescent complexes with $Eu^{3+}$. Five of these chelators can also form fluorescent complexes with $Tb^{3+}$, as set out in Table 1. Only chelator FSA has been found to be unique for $Tb^{3+}$ (17–19). Chelator VII was better, in terms of fluorescence intensity under the conditions of measurement, with $Tb^{3+}$ in comparison to $Eu^{3+}$. Two chelators, III and IV exhibited the property of working in the presence of excess EDTA; i.e., they form fluorescent complexes with $Eu^{3+}$ and $Tb^{3+}$ chelated to EDTA. This property is also seen with chelator FSA (17–19). In all other cases, fluorescence of the complexes decreases dramatically in the presence of EDTA. For all the chelators, the fluorescence measured is long-lived and lanthanide-specific. Native chelator fluorescence may also exist but is not detected by the time-resolved fluorometer.

Fluorescence intensity of the complexes varies with pH as shown in Table 1. However, solutions of $Eu^{3+}$ and $Tb^{3+}$ in buffers of alkaline pH deteriorate quickly due to hydroxide precipitation. For this purpose, complexes are preferably formed with the addition of an aqueous solution of $Eu^{3+}$ or $Tb^{3+}$ (pH ~6.5) which is stable for long periods of time at room temperature. In the cases of chelators III and IV, the $Eu^{3+}$ and $Tb^{3+}$ solutions were made in the presence of excess EDTA at pH 11. These solutions were also very stable when stored at room temperature. The fluorescence intensity of the complexes was highest when the $Eu^{3+}$ and $Tb^{3+}$ concentration in the final solution was around $2 \times 10^{-3}$ mol/L. Lower concentrations resulted in lower fluorescence signals.

The stability of fluorescence intensity with time was studied. Fluorescence intensity remained stable (±10%) for at least 3 h in the case of chelators II, III, IV, V, VII and IX and $Eu^{3+}$ and/or $Tb^{3+}$.

Fluorescence intensity decreased with time (change $\geq$ 10% per hour) in the case of chelators I, VI, VIII and X. This decrease was also noticed for FSA and previously reported (18).

Calibration curves with all chelators that form highly fluorescent complexes with $Eu^{3+}$ and/or $Tb^{3+}$ were constructed and the detection limits were calculated as the concentration that could be distinguished from zero with 95% confidence. The detection limits are reported in Table 1. Representative calibration curves are shown in FIG. 1. In all cases but one, detection limits were $<10^{-8}$ mol/L. Some chelators were clearly superior to FSA chelators in terms of detectability. Chelator FSA has already been used as a phosphate ester to devise highly sensitive immunoassays (18,19).

The modification of the structures of these chelators i.e. transformation into phosphate esters or galactosides can provide desired spectroscopic changes and/or chelation changes and/or energy transfer changes, the net result being an increase or loss of fluorescence in the presence of the lanthanides depending on the desired effect. A phosphate ester may be formed by utilizing the hydroxyl group of the chelator and a suitable reagent, such as, phosphoryl chloride or phosphorus pentachloride. Example 3 demonstrates an aspect of the invention in that HTQC emits excellent fluorescence, whereas the phosphate ester of HTQC has a much lower level of fluorescence. Line 2, Fraction 6 of FIG. 5, which is HTQCP, exhibits poor fluorescence. The HTQCP mixture includes a small amount of HTQC which is shown to elute at Fraction 21. The peak of line 1 of FIG. 5 is the fluorescence of the enzymatically treated substrate; namely, HTQCP of Fraction 6, reacted with the alkaline phosphatase to produce HTQC. The HTQC of line 1 produces far greater fluorescence as compared to HTQCP.

It is also understood that substitution of various entities of the compounds of formulae I to X may be done to enhance performance. Such substitutions may be with existing radicals or at other positions about the ringed structure. Such substitution may be in regard to other halogen groups, other alkyl groups and other alkaline groups and the like.

Another interesting application of the invention is to have a pair of compounds A and B one of which, A, is an enzyme substrate that forms fluorescent complexes with $Eu^{3+}$ or $Tb^{3+}$. Upon enzymatic cleavage of a group from A, which is then transformed to B, the ability of A to form fluorescent complexes is lost. One such pair reported here for the first time is X, 4-methylumbilliferylphosphate (4-MUP) and 4-methylumbelliferone (4-MU). Only X forms long-lived, highly fluorescent complexes with $Eu^{3+}$.

Figure 2A:
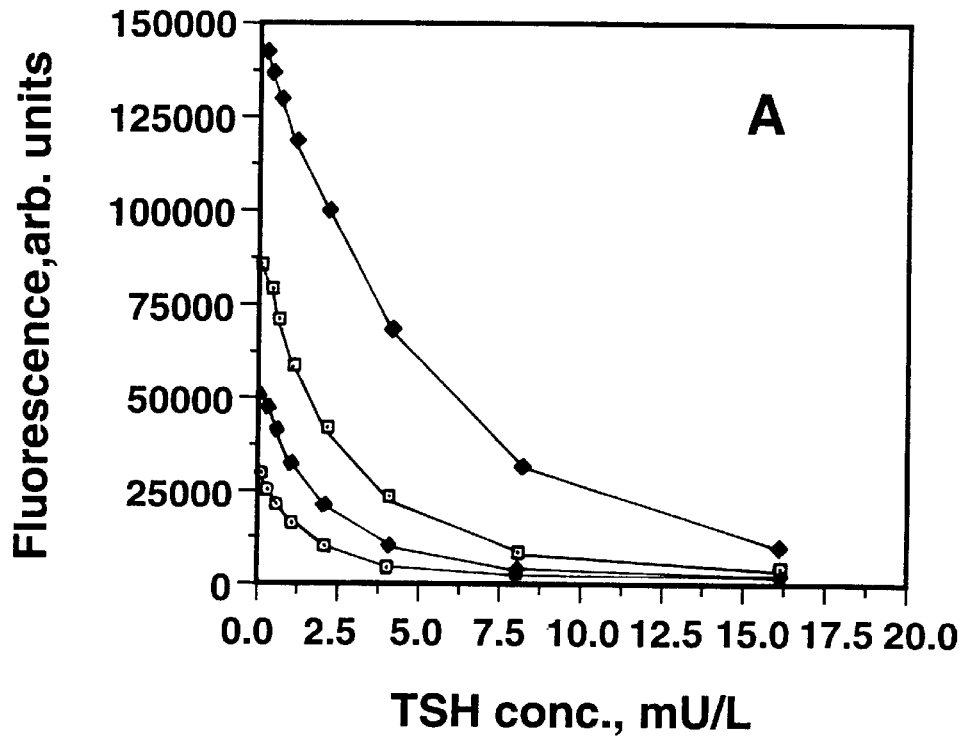
FIG. 2. Calibration curves for the proposed TSH assay (A). Fluorescence vs TSH concentration on linear axes (B). A percentage plot, where Bo is the fluorescence of the zero standard and B the fluorescence of all other standards. The concentration of the substrate used was (in mol/L from bottom to top): $5 \times 10^{-6}$; $1 \times 10^{-5}$; $2 \times 10^{-5}$; $5 \times 10^{-5}$.
Figure 2B:
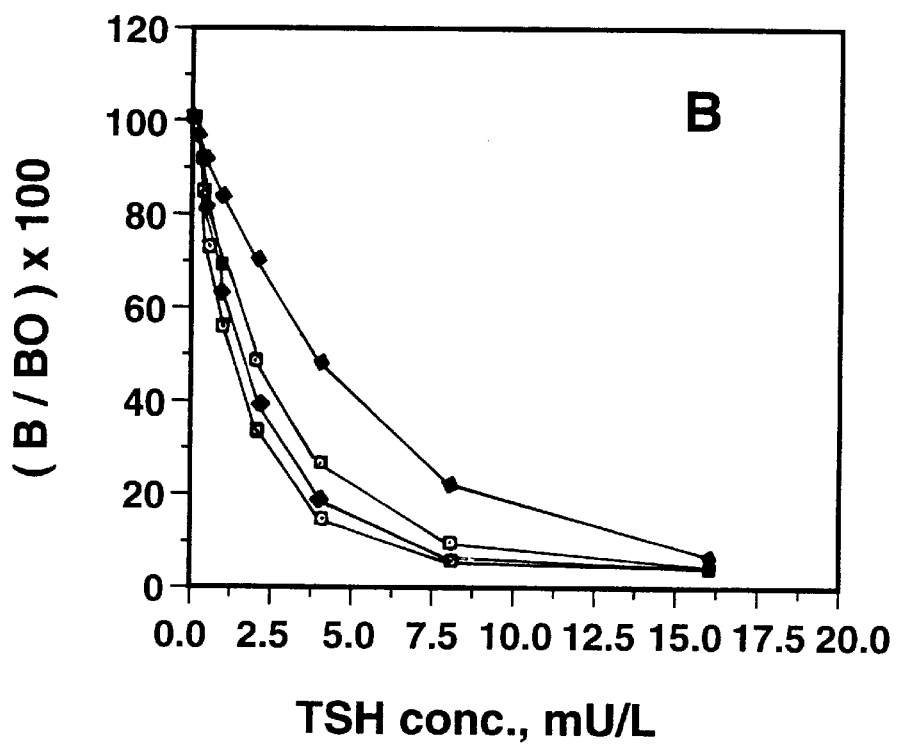

When ALP cleaves-off phosphate to produce 4-MU, the latter does not exhibit long-lived fluorescence in the presence of $Eu^{3+}$. In the absence of $EU^{3+}$ 4-MUP is a non-fluorescent ALP substrate. When ALP cleaves-off phosphate, the product, 4-MU, exhibits blue, short-lived fluorescence. The pair 4-MUP, 4-MU and $Eu^{3+}$ were used to develop two model time-resolved fluorometric immunoassays for TSH and T4 in serum. The design of the TSH assay is of the non-competitive heterogeneous immunoassay format where an immunocomplex of the type solid-phase-coating antibody-TSH-detection antibody-biotin-streptavidinalkaline phosphatase, is formed in polystyrene microtiter wells. The activity of ALP can then be measured in a number of different conventional ways. In this work, we detected ALP by adding the substrate X for 30 min, followed by addition of a $4 \times 10^{-3}$ mol/L $Eu^{3+}$ solution to form the fluorescent complex with the unreacted substrate. The calibration curves obtained are shown in FIG. 2. The sensitivity and range of assay can be adjusted by adjusting the concentration of the substrate added.

It is important to note that by this particular selection of substrates, the shape of the calibration curve with this substrate, is unique for this type of assay. Usually, the more the analyte in the sample, the more the signal observed; thus, cal. curves show proportionality between analyte concentration and signal. In the system of this invention, there is an inverse relationship between TSH concentration and signal, as shown in FIG. 2. This is due to the fact that the more the ALP present in the immunocomplex, the less the signal observed with the proposed substrate. The detection limit of the TSH assay is about 0.1 mU/L. Precision of this particular embodiment was excellent at 2–3% within the measuring range.

In comparison to conventional systems, it is possible to use the above principle for the 'competitive-type' heterogeneous assay formats which traditionally have calibration curves of the shape shown in FIG. 2 i.e. there is an inverse relationship between analyte concentration and signal. In the system according to an embodiment of this invention, the curves would show proportionality between analyte concentration and signal because high alkaline phosphatase concentration is associated with low signal.

Figure 3A:
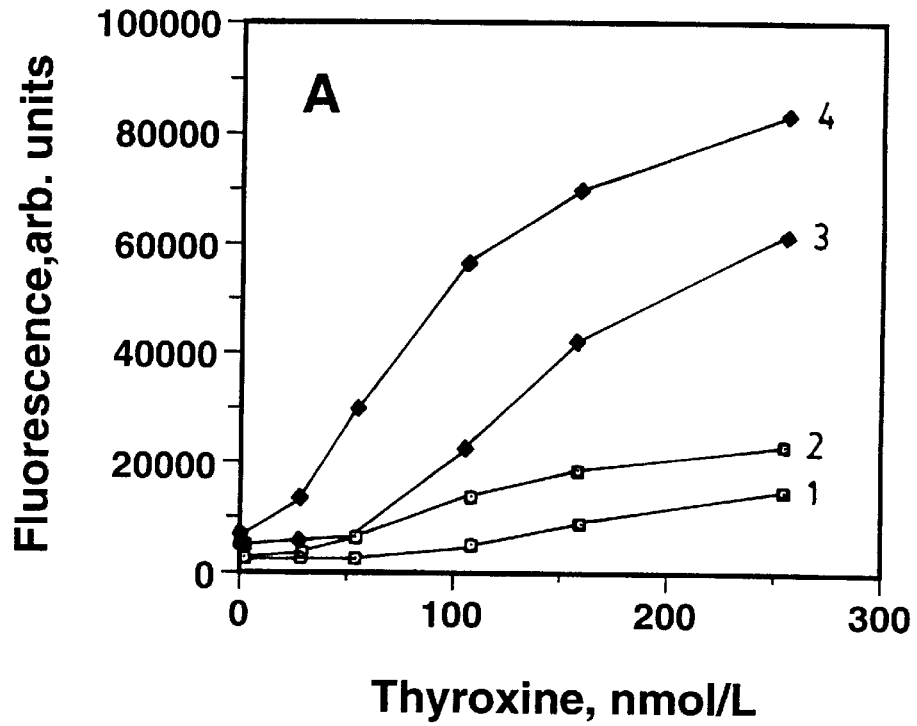
FIG. 3. Calibration curves for the proposed thyroxine assay (A). Double linear plots. (B) Double logarithmic plots. The substrate concentration and antibody dilutions used were: $5 \times 10^{-6}$M and 10-fold (1); $5 \times 10^{-6}$M and 20-fold (2); $2 \times 10^{-5}$M and 10-fold (3); $2 \times 10^{-5}$M and 20-fold (4).
Figure 3B:
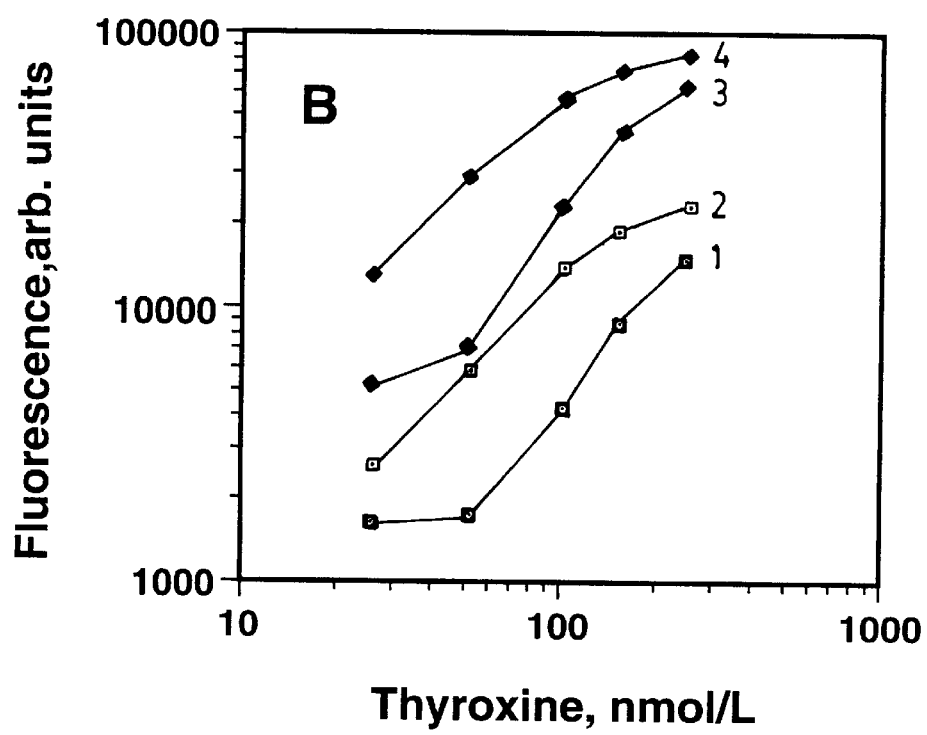
Figure 4:
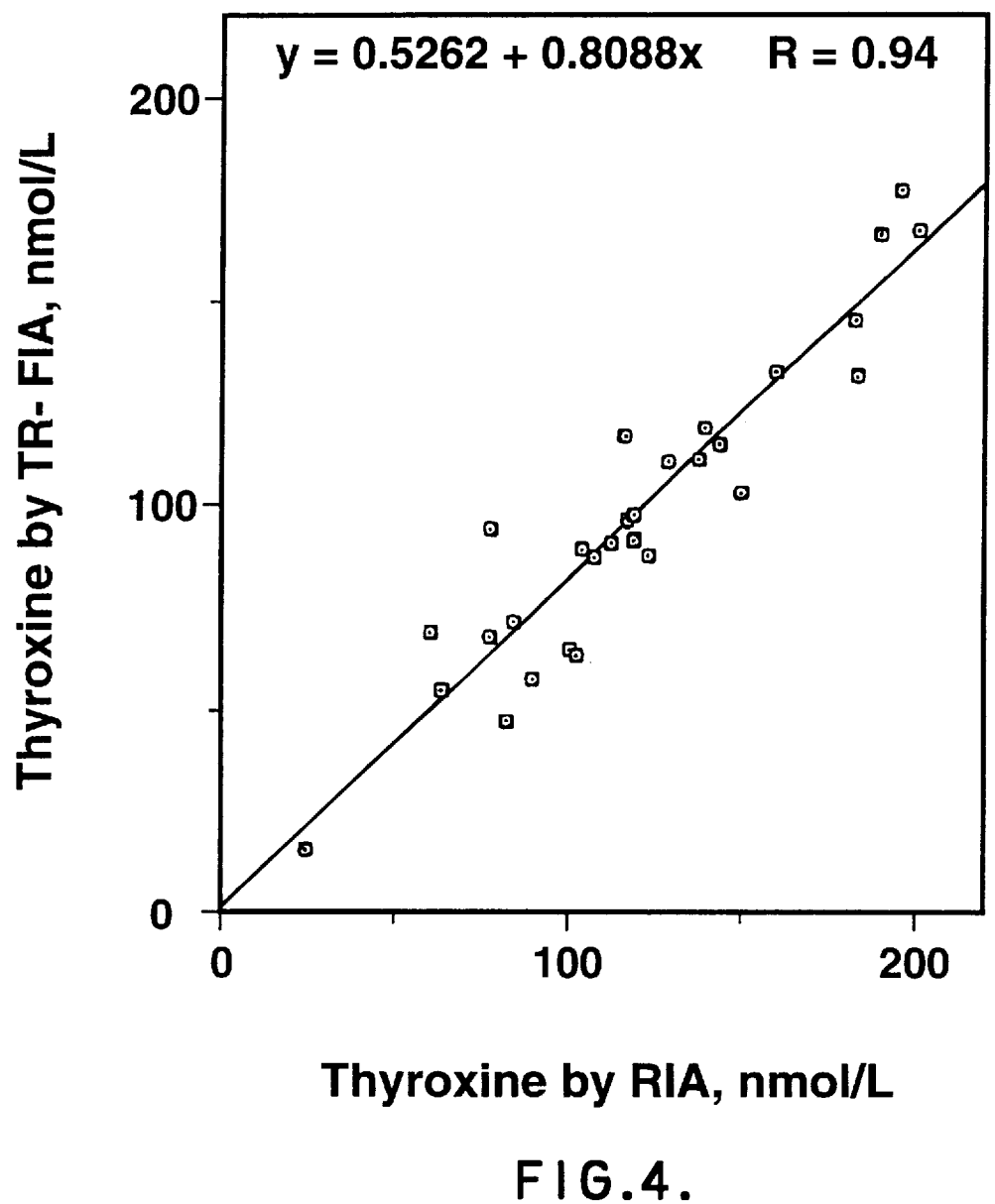
FIG. 4. Correlation between serum thyroxine results obtained with a radioimmunoassay (RIA) and the proposed assay method, time resolved fluorometric immunoassay (TR-FIA).

To demonstrate this, a competitive assay for T4 was designed as follows: Polystyrene microtiter wells were coated with a T4protein conjugate as described previously (20). In the assay, T4 in the sample competes with immobilized T4 for binding to a biotinylated anti-T4 monoclonal antibody. After washing out excess reagents, we added a SA-ALP conjugate to form the immunocomplex: solid-phase-T4antibodybiotin-SA-ALP. The activity of ALP can then be quantified with use of the substrate, X. With a conventional detection system, the amount of signal generated by ALP is inversely related to the analyte concentration and the calibration curves have a shape similar to those of FIG. 2. In this alternative system, there is a direct relationship between signal and analyte concentration. Calibration curves obtained with the system are shown in FIG. 3. Sensitivity can be adjusted by changing the antibody dilution, the substrate concentration and the substrate incubation time. Under optimised conditions, 10 clinical samples have been analyzed by the method of this invention and by a conventional radioimmunoassay procedure. The comparison is shown in FIG. 4. A good correlation exists between the two methods. Additionally, precision studies with three samples gave the following results (N=12): T4 of 112 nmol/L, RSD (relative standard deviation)=8.1 %; 59 nmol/L, RSD 6.2%; 25.9 nmol/L, 8.2%. Samples diluted 2-fold or 4fold gave values between 93–105% of expected results confirming a good linearity of the proposed procedure.

Enzymatically amplified time-resolved fluorescence immunoassays exhibit excellent sensitivity and can be used for the routine manual or automated assay of many analytes in biological fluids. The first system reported, is based on alkaline phosphatase and the substrate 5-fluorosalicyl phosphate (FSAP) in combination with $Tb^{3+}$ (17–19). Other possible chelators can be used which offer better detectability in comparison to FSA. Moreover, some of these chelators form stable complexes with $Eu^{3+}$ and $Tb^{3+}$ thus being advantageous to the previously reported system in which fluorescence decays with time.

A unique system based on the pair 4-methylumbilliferyl phosphate (4-MUP) of formula X and 4-methylumbelliferone (4-MU) in combination with $Eu^{3+}$ has been demonstrated. This pair works in the exact opposite way in comparison to the reported FSAP-FSA-$Tb^{3+}$ system (17–19). Here, 4-MUP forms the fluorescent complex with $Eu^{3+}$, cleavage of phosphate by alkaline phosphatase releases 4-MU which does not form fluorescent complexes with $Eu^{3+}$. This system works well in both 'non-competitive-type' and 'competitive-type' immunoassays. Its advantage in comparison to the conventional methodologies is mainly in competitive-type assays in which the calibration curve shows a direct relationship between analyte concentration and signal. In this case, assay sensitivity is superior because of the much larger signal ratios obtained between the first two standard points of the calibration curve. This system can thus be used in combination with the previously described system (17–19) to devise immunoassays that show a direct relationship between signal and analyte concentration irrespective of the immunoassay type used (competitive or non-competitive).

Although preferred embodiments of the invention are described herein in detail, it will be understood by those skilled in the art that variations may be made thereto without departing from the spirit of the invention or the scope of the appended claims.

TABLE 1

Optimal Assay Conditions of Chelators in the Presence of $Eu^{3+}$ or $Tb^{3+}$

| | Works in presence of EDTA? | Detection Limit, Mol/L | Stability of Fluorescence | pH optimum[2] |
|---|---|---|---|---|
| Europium Chelator | | | | |
| I | No | $5 \times 10^{-9}$ | Poor | 11 |
| II | No | $5 \times 10^{-9}$ | Good | 9–11 |
| III | Yes | $2 \times 10^{-9[1]}$ | Good[1] | 11[1] |
| IV | Yes | $2 \times 10^{-9[1]}$ | Good[1] | 11[1] |
| V | No | $2.5 \times 10^{-9}$ | Good | 11 |

TABLE 1-continued

Optimal Assay Conditions of Chelators in the Presence of $Eu^{3+}$ or $Tb^{3+}$

| | Works in presence of EDTA? | Detection Limit, Mol/L | Stability of Fluorescence | pH optimum[2] |
|---|---|---|---|---|
| VI | No | $2.5 \times 10^{-9}$ | Poor | 9–11 |
| VII | No | $4 \times 10^{-9}$ | Good | 9–11 |
| VIII | No | $7 \times 10^{-9}$ | Poor | 11 |
| IX | No | $2.5 \times 10^{-9}$ | Good | 9–11 |
| X | No | $2.5 \times 10^{-9}$ | Poor | 9–11 |
| Terbium Chelator | | | | |
| II | No | $5 \times 10^{-9}$ | Good | 11 |
| III | Yes | $3'3\ 10^{-9[1]}$ | Good[1] | 11[1] |
| IV | Yes | $5 \times 10^{-9[1]}$ | Good[1] | 11[1] |
| VII | No | $2 \times 10^{-9}$ | Good | 11 |
| X | No | $3.9 \times 10^{-9}$ | Poor | 11 |

[1]Studies done in the presence of $Eu^{3+}$ or $Tb^{3+}$ and EDTA
[2]Solutions of $Eu^{3+}$ and $Tb^{3+}$ are stable at alkaline pH only in the presence of excess EDTA. Detection limits were thus established at optimal pH only for chelators III and IV. In all other cases, aqueous solutions of $Eu^{3+}$ and $Tb^{3+}$ of pH 6.5 were used as described.

(2) Solutions of $Eu^{3+}$ and $Tb^{3+}$ are stable at alkaline pH only in the presence of excess EDTA. Detection limits were thus established at optimal pH only for chelators III and IV. In all other cases, aqueous solutions of $Eu^{3+}$ and $Tb^{3+}$ of pH 6.5 were used as described.

We claim:

1. In a time resolved fluorometric assay comprising the steps of:

enzymatically treating a substrate to form a fluorescent lanthanide metal chelate in the presence of a lanthanide metal ion and detecting the fluorescence emitted, the improvement comprising forming a fluorescent lanthanide metal chelate between either $Eu^{3+}$ or $Tb^{3+}$ and an enzymatically treated substrate selected from the group consisting of: 3-hydroxypicolinic acid; 4-hydroxy-7-methyl-1,8-naphthyridine-3-carboxylic acid; 3-hydroxy-2-quinoxaline carboxylic acid; 7-hydroxycoumarin-4acetic acid; calcein blue; 2-quinoxaline carboxylic acid; pterin-6-carboxylic acid; and 4methylumbelliferyl phosphate.

2. The assay of claim 1 wherein the fluorescent lanthanide metal chelate is formed between $Eu^{3+}$ and said enzymatically treated substrate.

3. The assay of claim 1 wherein the fluorescent lanthanide metal chelate is formed between $Tb^{3+}$ and said enzymatically treated substrate.

4. In a time-resolved fluorometric assay, comprising the steps of:

enzymatically treating a substrate to form a lanthanide metal chelate in the presence of a lanthanide metal ion and detecting the fluorescence emitted, the improvement comprising the use of a substrate from the group consisting of those with the following formulae II, IV, V, VI, VII, VIII, IX, and X:

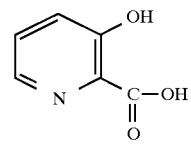

II

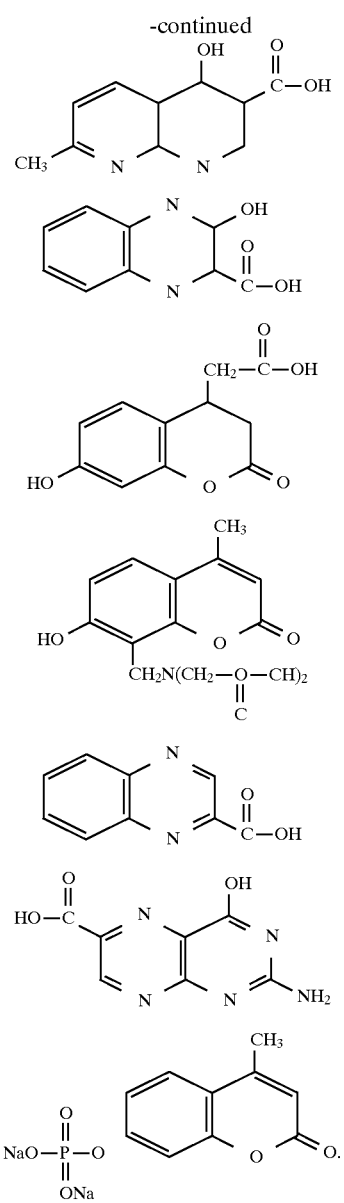

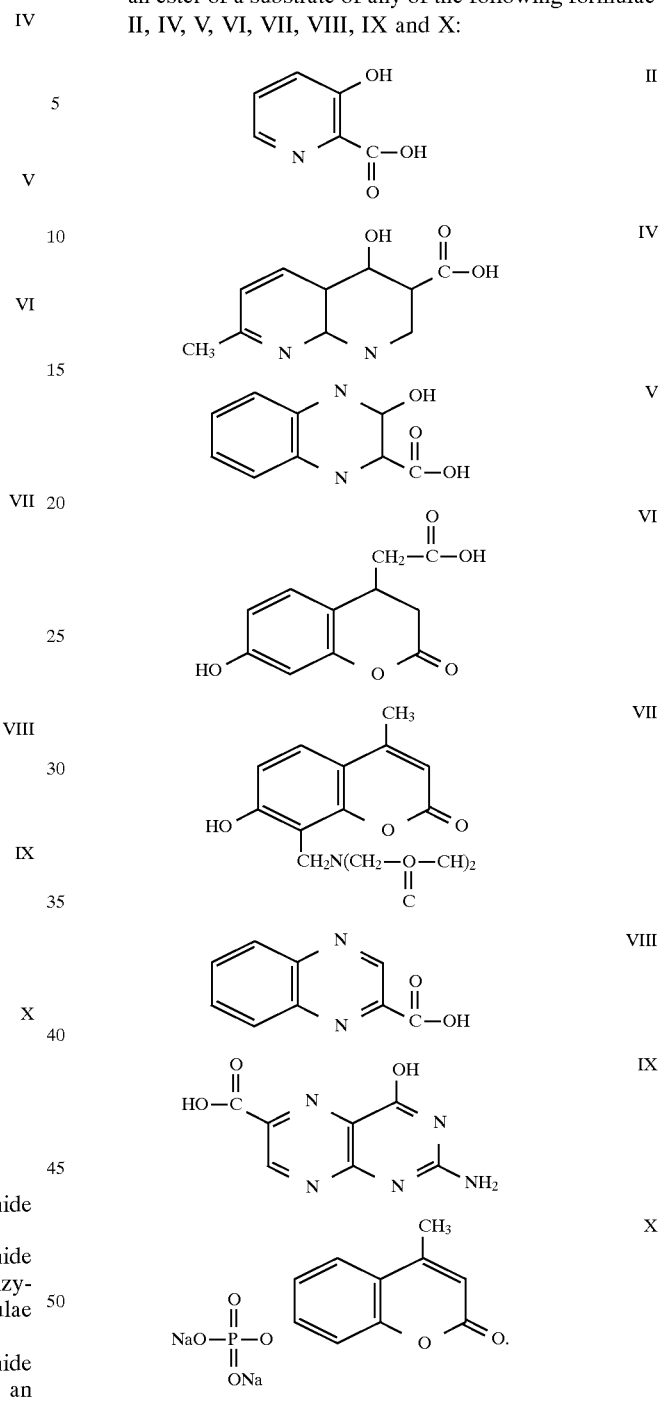

5. The assay according to claim 4, wherein said lanthanide metal ion is an ion of europium or terbium.

6. The assay according to claim 5, wherein said lanthanide metal chelate is made from an ion of europium and enzymatically treated substrate selected from those of formulae II, IV, VII and IX.

7. The assay according to claim 5, wherein said lanthanide metal chelate is made from an ion of terbium and an enzymatically treated substrate selected from those of formulae II, IV, VII and IX.

8. In a time resolved fluorometric assay, comprising the steps of:

enzymatically treating an ester of a substrate to form a lanthanide metal chelate in the presence of a lanthanide metal ion to render the lanthanide metal chelate as either fluorescent or non-fluorescent when combined with the lanthanide metal and detecting the fluorescence emitted, the improvement comprising the use of an ester of a substrate of any of the following formulae II, IV, V, VI, VII, VIII, IX and X:

9. The assay of claim 8, wherein said esters are selected from phosphate and galactoside esters.

10. The assay of claim 9, wherein said esters are phosphate esters.

11. The assay of claim 8, wherein the enzymatically treated ester of formula X is 4-methylumbelliferyl phosphate which forms a fluorescent chelator with a lanthanide metal.

* * * * *